(12) United States Patent
Chi et al.

(10) Patent No.: US 9,532,960 B2
(45) Date of Patent: Jan. 3, 2017

(54) PHARMACEUTICAL COMPOSITION AND KIT FOR APPLYING METFORMIN AND SODIUM BUTYRATE IN KRAS MUTATION CANCER TREATMENT

(71) Applicant: Uropro Biotech Co., Ltd, Taipei (TW)

(72) Inventors: Kwan-Hwa Chi, Taipei (TW);
Yu-Shan Wang, Taipei (TW);
Chao-Chun Chang, New Taipei (TW)

(73) Assignee: JOHNPRO BIOTECH INC., New Taipei (TW)

( * ) Notice: Subject to any disclaimer, the term of this patent is extended or adjusted under 35 U.S.C. 154(b) by 336 days.

(21) Appl. No.: 14/157,873

(22) Filed: Jan. 17, 2014

(65) Prior Publication Data

US 2014/0343144 A1 Nov. 20, 2014

(30) Foreign Application Priority Data

May 14, 2013 (TW) .............................. 102117107 A

(51) Int. Cl.
*A61K 31/155* (2006.01)
*A61K 31/20* (2006.01)
*A61K 31/19* (2006.01)

(52) U.S. Cl.
CPC ............. *A61K 31/19* (2013.01); *A61K 31/155* (2013.01)

(58) Field of Classification Search
CPC .............................. A61K 31/155; A61K 31/19

USPC .................................................. 514/635, 558
See application file for complete search history.

(56) References Cited

U.S. PATENT DOCUMENTS 5,858,024 A * 1/1999 De Lacharriere ........ A61K 8/20
424/70.6

OTHER PUBLICATIONS

Umene et al., "New candidate therapeutic agents for endometrial cancer: Potential for clinical practice (Review)", Oncology Reports, vol. 29, No. 33, pp. 855-860 (Jan. 2013).*
Cooney, Craig A., "Drugs and supplements that may slow aging of the epigenome", Drug Discovery Today: Therapeutic Strategies, 2010, vol. 7, No. 3-4, pp. 57-64.

* cited by examiner

*Primary Examiner* — Kevin E Weddington
(74) *Attorney, Agent, or Firm* — Muncy, Geissler, Olds & Lowe, P.C.

(57) ABSTRACT

A method for using metformin and sodium butyrate in combination to treat a cancer patient with K-ras mutation is disclosed. When administering the pharmaceutical composition to a cancer patient, Metformin and sodium butyrate offer cooperatively therapeutic efficacy. The present invention also discloses a pharmaceutical composition and a pharmaceutical kit containing both aforementioned. The application of the method, the pharmaceutical composition and the pharmaceutical kit of the present invention are advantageous for improving the treatment effect to cancer patients with K-ras mutation.

10 Claims, 2 Drawing Sheets

PHARMACEUTICAL COMPOSITION AND KIT FOR APPLYING METFORMIN AND SODIUM BUTYRATE IN KRAS MUTATION CANCER TREATMENT

CROSS REFERENCE TO RELATED APPLICATIONS

This Non-provisional application claims priority under 35 U.S.C. §119(a) on Patent Application No(s). 102117107 filed in Taiwan, Republic of China on May 14, 2013, the entire contents of which are hereby incorporated by reference.

BACKGROUND OF THE INVENTION

Field of Invention

This invention relates to a pharmaceutical composition, a pharmaceutical kit and a method.

Related Art

Metformin is isolated from *Galega offivinalis*, and *Galega officinalis* was used for the treatment of diabetes for centuries. In the 1920s, the guanidine compound was discovered in Galega extracts, and, by animal experiments, the guanidine compound has been confirmed to be the main active ingredient to reduce blood glucose concentration. So far, we've known the mechanism of metformin or the medically acceptable salt thereof is to enhance glucose uptake and carbohydrates catabolism in muscle cells, and to suppress glucose production by the liver. Metformin thus has an antihyperglycemic effect, and has been widely used in treating type 2 (non-insulin dependent) diabetes mellitus.

Some patients with the type 2 diabetes mellitus have extraordinary high risk of having one of the three cancers at the same time: colorectal cancer, breast cancer and pancreatic cancer. Some studies show that administration of metformin or the pharmaceutically acceptable salt thereof can generally reduce the risk of developing cancer in the patients with type 2 diabetes mellitus. In other words, among the patients with type 2 diabetes mellitus, those who are administered with metformin or the pharmaceutically acceptable salt thereof have less risk of developing colorectal cancer, breast cancer or pancreatic cancer than those who are not administered.

On the other hand, the sodium butyrate is a histone deacetylase inhibitor (HDACi). The phenomenon of the histone deacetylase (HDAC) overexpression widely exists in many kinds of cancer; therefore, the sodium butyrate is considered as a substance with a great therapeutic potential, and applied in many cell or animal experiments. Current studies have found that the sodium butyrate inhibits growth of some specific cancer cell and induces apoptosis of some specific cancer cell; thereby the sodium butyrate has an efficacy of slowing tumor growth. Furthermore, sodium butyrate is also considered as a protective agent of the intestinal tract, which can repair the intestinal mucosa and treat the inflammation of the intestinal tract, thereby to reduce the risk of colitis oncogenesis. Furthermore, sodium butyrate also has been found to be able to prevent the developing of breast cancer.

In summary, currently studies confirm that metformin or the pharmaceutically acceptable salt thereof, or the sodium butyrate is individually effective for some specific cancer, to a certain degree. However, the therapeutic effect of each compound is only has their respective effect. Besides, metformin is still mostly used in the treatment of diabetes. As for reducing the morbidity of colorectal cancer, breast cancer or pancreatic cancer, due to the mechanism is not clear, and such efficacy has not been expected. Therefore, further studies of metformin and sodium butyrate still make no breakthrough for now.

However, especially for cancer patients with K-ras mutation, current drug has no significant therapeutic effect, and the clinical studies also confirm using metformin or the pharmaceutically acceptable salt thereof, or using sodium butyrate, is not much help for relieving or ameliorating the symptoms of the K-ras mutation cancer.

SUMMARY OF THE INVENTION

Only using metformin or the pharmaceutically acceptable salt thereof, or only using the sodium butyrate to some specific cancer and tumors has some efficacy, but still no research reports or literatures point out the combined use of metformin and sodium butyrate. However, applicants have found the therapeutic efficacy of combined use of metformin and sodium butyrate is much better than using metformin or sodium butyrate individually. Hence, the present invent discloses a pharmaceutical composition, kit and method for applying metformin and sodium butyrate, to improve the therapeutic efficacy of the K-ras mutation cancer.

In details, the present invention discloses a method for using a metformin and a sodium butyrate for treating a cancer patient with K-ras mutation, wherein when the pharmaceutical composition administered to the cancer patient, the metformin and the sodium butyrate offer cooperatively therapeutic efficacy. In the present invention, the method as mentioned also includes a use for using a metformin and a sodium butyrate for treating a cancer patient with K-ras mutation.

The present invention also discloses a pharmaceutical composition for treating a cancer patient with K-ras mutation, the composition comprising a metformin and a sodium butyrate, wherein when the pharmaceutical composition administered to the cancer patient, the metformin and the sodium butyrate offer cooperatively therapeutic efficacy.

The present invention also discloses a pharmaceutical kit for treating a cancer patient with K-ras mutation, the pharmaceutical kit comprising a metformin along with a first pharmaceutically acceptable carrier, diluent or excipient and a sodium butyrate along with a second pharmaceutically acceptable carrier, diluent or excipient, wherein when the pharmaceutical kit is administered to the cancer patient, the Metformin and the sodium butyrate offer cooperatively therapeutic efficacy.

In order to describe more clearly about the technical features of the present invention, the following defines some specific terms, and further illustrate the detail of the present invention. In the present invention, the metformin and sodium butyrate are used in combination for treating cancer patients with K-ras mutation, and "use (or used, using) . . . in combination" means using these two ingredients both: metformin and sodium butyrate. They can be made into a pharmaceutical composition, which includes both of the metformin and the sodium butyrate. They can also be made into a pharmaceutical kit (it also be called combined drug or combined medicine), which includes two kinds of medicine, one ingredient along with metformin and another ingredient along with sodium butyrate, and the two kinds of medicine are used at the same time. Preferably, the pharmaceutical composition or the pharmaceutical kit individually has an effective amount of metformin and an effective amount of sodium butyrate, wherein the effective amount means the dose of these two ingredients which are combined to use can produce synergistic effects.

The "K-ras mutation" used here means the mutation of a KRAS gene, which is a kind of oncogene, and the KRAS gene can be classified into the normal (or wide-type) KRAS gene and the mutant KRAS gene. The normal KRAS gene suppresses tumor growth, but the mutant KRAS gene promotes cell proliferation, and causes tumor generation. In addition, more studies show that K-ras mutation is found at high rates in lung cancer, pancreatic cancer and colon cancer. The generally therapeutic drugs for the treatment of above cancer patients are limited, thus, by the clinical tests, the cancer patients are divided into two categories: of non K-ras mutation and of K-ms mutation.

In addition, the "synergistic effect" herein means when using two or more substances in combination, it produces an effect greater than the sum of their individual effect (which includes producing the same efficacy or reducing the adverse reactions). The experiments of present invention show that the therapeutic efficacy with combined administrating metformin and sodium butyrate to the cancer patients with K-ras mutation is better than only using metformin or sodium butyrate individually.

The "treat" means it can reduce, relieve, ameliorate, improve, or affect cancer and the symptoms thereof, for example, inhibiting or treating pain or bleeding induced by cancer, or slow or reverse tumor progression.

The "metformin" means the metformin itself, and also includes the derivatives thereof which are chemically or biologically modified or substituted and still retain the same or similarity properties of metformin. Of course, the "metformin" also includes the medically acceptable salt of metformin, which is based on the acidic group or the base of its chemical structure, for example, the metformin hydrochloride.

Further, the compounds or substances which are mentioned and substantially related to the present invention, which include any pharmaceutically acceptable form thereof. The pharmaceutically acceptable form can be but not limited to the diastereomer, enantiomer and all types of isomers, salt, free form, solvent, prodrug, polymorph and racemic mixture thereof.

In the present invention, when the metformin and the sodium butyrate are used in combination, the metformin is administered preferably at a dose between 130 mg and 1,000 mg, and the sodium butyrate is administered preferably at a dose between 40 mg and 300 mg, and the weight ratio of the metformin to the sodium butyrate is 4:1 (the ratio in molarity is 2.67:1). Of course, the above administered dose and weight ratio can also be the compositing ratio of the ingredients in the pharmaceutical composition, or the compounding ratio of the pharmaceutical kit when actual used.

In the present invention, the cancer patients with K-ras mutation can be not limited to lung cancer patients, pancreatic cancer patients, rectal cancer patients or colon cancer patients with K-ras mutation, for treating tumors, delaying tumor progression or prevent tumor generation.

In the present invention, when the metformin and the sodium butyrate are used in combination, both cooperatively modulate the metabotropic glutamate signaling pathway in cancer cells to treat the cancer patient.

As mentioned above, the method, the pharmaceutical composition and the pharmaceutical kit of the present invention, based on using the metformin and sodium butyrate in combination, are advantageous for improving the treatment effect to cancer patients with K-ras mutation.

BRIEF DESCRIPTION OF THE DRAWINGS

The present invention will become more fully understood from the subsequent detailed description and accompanying drawings, which are given by way of illustration only, and thus are not limitative of the present invention and wherein.

DETAILED DESCRIPTION OF THE INVENTION

Figure 1:
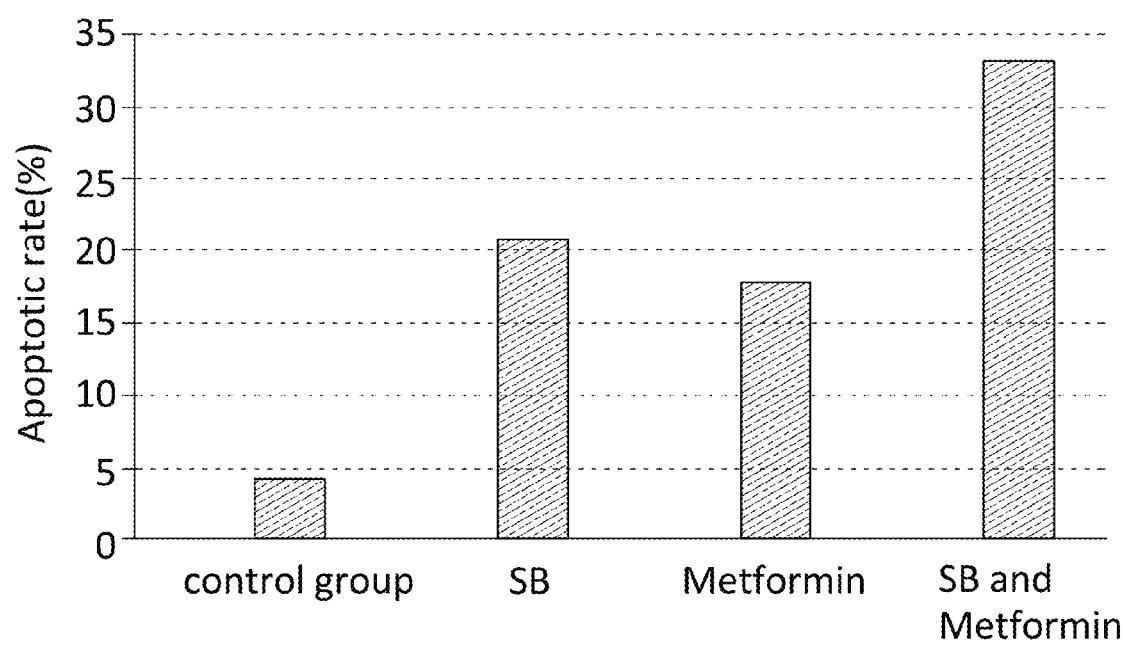
FIG. 1 is a bar chart illustrating the apoptosis results of the treated HCT116 cells analyzed by flow cytometer according to experiment 2.

The present invention will be apparent from the following detailed description, which proceeds with reference to the accompanying drawings, wherein the same references relate to the same elements.

The present invention discloses a method for using metformin and sodium butyrate for treating a cancer patient with K-ras mutation. In the embodiment, metformin and sodium butyrate can be made into a pharmaceutical composition, and then the pharmaceutical composition is administered to patients. And the synthesis methods of metformin and sodium butyrate are well-understood by the person having ordinary skill in the art, and are not repeated here. The pharmaceutical composition above mentioned can be in a solid, liquid or half-liquid dosage form, and the present invention is not limited to this way. When applying in solid dosage form, preferably, the metformin and the sodium butyrate are uniformly mixed to make a tablet, which is advantageous to pharmaceutical effect. But in the solid dosage form, the metformin and the sodium butyrate are not limited to uniformly mixed. In other words, in the same dosage form of the pharmaceutical composition, the metformin and the sodium butyrate can be mixed to a degree rather than uniformly, even can be unmixed. For example, the pharmaceutical composition can be made as a tablet or capsule, and one part of it is metformin, and the other part of it is sodium butyrate. Preferably, in other embodiments, the commercial metformin powder and sodium butyrate powder can directly be bought from the manufactures as raw materials, and the pharmaceutical composition is made as a powder agent by mixing both powder of metformin and sodium butyrate.

Of course, for the convenience of manufacture, packaging or administration, the pharmaceutical composition preferably may comprise a pharmaceutically acceptable carrier, diluent, excipient or combination thereof, to facilitate the manufacture of the suitable combined dosage form or recipe form. Wherein, the pharmaceutically acceptable carrier, diluent or excipient, for example, can be a known magnesium carbonate, magnesium stearate, talc, sugar, lactose, or combinations thereof.

Generally, the suitable dose range of metformin for treating cancer is well-understood by the person having ordinary skill in the art, which is also the applied dose range of metformin when metformin and sodium butyrate are used in combination for treatment. For example, the recommended daily dose of metformin is between 0.2 mg and 2,000 mg per kilogram of body weight of the cancer patient with K-ras mutation; when used in combination, the dose of metformin is preferably controlled between 130 mg and 1,000 mg, and the dose of sodium butyrate is preferably controlled between 40 mg and 300 mg. Within the above range, the therapeutic efficacy of various doses might have considerable gaps between each other. So that, the preferable dose for treatment can be referred to the following experiments, in which the weight ratio of the metformin to the sodium butyrate is 4:1.

Of course, the dose of metformin or sodium butyrate may change with the active ingredient, administrating route or individual needs and physiological condition. In general, the oral administration needs high dose, but the dose used in the early treatment is relatively low.

Each recipe may contain a dosage unit of the pharmaceutical composition. In other words, a recipe contains sufficient dose to generate therapeutic efficacy for treating a cancer patient with K-ras mutation, to facilitate direct administering. In the embodiment, each powder agent contains a dosage unit of the pharmaceutical composition. Of course, in other embodiments, a dosage unit may also be consisted of a plurality of pharmaceutical compositions which are dispended into many sub-units or sub-packages, For example, it is dispended into two to three tablets or capsules, which are packaged in the same blister pack.

Furthermore, according to the method of the present invention, when the pharmaceutical composition is administered to the cancer patient, metformin and sodium butyrate produce synergistic effect, to improve or enhance the therapeutic efficacy of individually using metformin or sodium butyrate to treat the cancer patients with K-ras mutation. Then, it reaches to eliminate, inhibit, improve, ameliorate, relieve, or prevent the cancers and the symptoms thereof, or delay, stop, reverse tumor progression, or achieve the similar medical effects of the above objects.

The present invention also discloses a pharmaceutical composition for treating a cancer patient with K-ras mutation, the composition comprising a metformin and a sodium butyrate. However, the pharmaceutical compositions are substantially the same with pharmaceutical compositions above mentioned, and it can be referred to the aforementioned, and is not repeated here.

The present invention also discloses a pharmaceutical kit, which comprising a metformin along with a first pharmaceutically acceptable carrier, diluent or excipient and a sodium butyrate along with a second pharmaceutically acceptable carrier, diluent or excipient. Wherein, metformin, sodium butyrate and other relative descriptions can be referred as aforementioned, and the insufficient or unexplained part will be illustrated here.

The first or second pharmaceutically acceptable carrier, diluent, excipient or the combination thereof can be substances or materials understood in the technical field of the present invention, and the manufacturing method to combine metformin and sodium butyrate and the dosage form thereof, are well-understood by the person having ordinary skill in the art. And in a embodiment, the pharmaceutical kit have separate packages or containers, such as blister packs, respectively receiving or storing the tablets made by metformin along with a first pharmaceutically acceptable excipient and the tablets made by sodium butyrate along with a second pharmaceutically acceptable excipient, for offering patients to take at the same time, or administering to patients after modulated. Particularly, the pharmaceutical kit is limited to use metformin and sodium butyrate in combination. However, the use in combination might be either the metformin or the sodium butyrate is first administered to the patients, and before losing the efficacy thereof, the other is administered to the patients. The time lapse between the two substances are administered can be 1 hour to 3 days. It is preferable to administer both of the substances at the same time to patients, or administer one of the substances then immediately administering the other.

As mentioned above, according to the method, the pharmaceutical composition and the pharmaceutical kit of the present invention, using the metformin and sodium butyrate in combination is advantageous for improving the treatment effect to cancer patients with K-ras mutation.

Experiment 1: Preparation of Pharmaceutical Composition

In the present invention, metformin was purchased from China Chemical & Pharmaceutical Co., Ltd., Taiwan, and sodium butyrate was purchased from Merck Ltd., Taiwan. About 331 mg of metformin (2 mM) and about 83 mg of (0.75 mM) of sodium butyrate was weight in ambient temperature, and then metformin powder and sodium butyrate powder was mixed in a weight ratio of the metformin to the sodium butyrate that is 4:1 (the ratio in molarity is 2.67:1), which is a dosage unit. Then, the dosage unit is packaged as a powder agent or into a cachet, and stored at room temperature.

Experiment 2: The Pharmaceutical Composition of Metformin and Sodium Butyrate has Synergistic Effect on Cancer Cells' Apoptosis The human colon cancer cell HCT116 (cell line with K-ras mutation) is cultured in the McCoy's 5A with 10% fetal bovine serum. When the HCT116 cells are cultured to the appropriate number, then the adherent HCT116 cells are suspended, and $2.5 \times 10^5$ HCT116 cells per well are seeded in a 6-wells dish. After incubated for 12 hours, sodium butyrate with a final concentration of 0.75 mM, metformin with a final concentration of 2 mM, and the pharmaceutical composition with final concentration of 0.75 mM metformin and 2 mM sodium butyrate are respectively added to the 6-wells dish as above mentioned.

In this embodiment, the final concentration as mentioned means the concentration of respective substances after added in the medium for cell culture, and therefore the medium respectively contains 0.75 mM sodium butyrate, 2 mM metformin, or 0.75 mM sodium butyrate and 2 mM metformin.

After respectably added the above compounds to HCT116 cells, the 6-well dish is incubated in an incubator of 37° C. for 72 hours. After that, the medium and compounds in each well are sequentially removed, and each well is washed by Phosphate Buffered Saline (PBS), then the HCT116 cells are harvested, by treating trypsin-EDTA, for apoptosis analysis.

The apoptosis analysis is based on the Annexin V apoptosis detection kit (BD Pharmingen) for analysis the exposure of phosphatidylserine, and the protocol follows the accompanying manual. In brief, the treated HCT116 cells are washed three times with PBS, and then immediately stained with Annexin V/Propidium Iodide (PI). 1% fetal bovine serum albumin (BSA) is first added to the treated cells. After subsequently added 222.5 µl of binding buffer, 10 µl of PI and 2.5 µl of Annexin V-FITC are directly then added to stain the cells, followed by immediate incubation for 10 minutes at low temperature in the dark. The percentage of the apoptosis is calculated by the flow cytometry and FACSCalibur, the analysis software thereof.

FIG. 1 is a bar chart illustrating the apoptosis results of the treated HCT116 cells according to experiment 2. With reference to FIG. 1, the bar labeled with "control group" represents the apoptotic rate of HCT116 cells treated by the same processing steps but without adding metformin and sodium butyrate, and the bar labeled with "SB" or "Metformin" represents the apoptotic rate of HCT116 cells treated by the same processing steps but only added either sodium butyrate (SB) or metformin, and the bar labeled with "SB and Metformin" means adding both of sodium butyrate and Metformin. The bar chart shows that the apoptotic rate of HCT116 cells only added either sodium butyrate (SB) or metformin increases to about 20%, which is improved about 15% compared to the control group. Moreover, when using the sodium butyrate and the metformin in combination, the apoptotic rate of HCT116 cells increases to 35%, which is significantly improved about 30% compared to the control group. Therefore, according to the experiment 2, it shows that the pharmaceutical compositions using metformin and sodium butyrate in combination do have better toxic effect, resulting in increasing apoptotic rate, due to the synergistic effect of using sodium butyrate and metformin in combination.

Experiment 3: The Apoptosis in Cancer Cells Treated by Pharmaceutical Compositions with Different Final Concentration of Metformin and Sodium Butyrate The protocol and conditions are almost the same as experiment 2, but different doses (concentrations) of sodium butyrate, metformin, or the pharmaceutical composition of metformin and sodium butyrate are used to treat HCT116 cells. In this experiment, for easy to understanding, the group of only using sodium butyrate to treat the HCT116 cells is called group A, and the group of only using metformin to treat the HCT116 cells is called group B, and the group of using the pharmaceutical compositions of metformin and sodium butyrate to treat the HCT116 cells is called group C as follows, wherein, groups A, B and C are further divided into seven subgroups with different concentrations (in this experiment, that means final concentration), as shown in the following table:

| Number | A1 | A2 | A3 | A4 | A5 | A6 | A7 |
|---|---|---|---|---|---|---|---|
| Sodium butyrate (mM) | 3 | 1.5 | 0.75 | 0.375 | 0.188 | 0.094 | 0.047 |
| Number | B1 | B2 | B3 | B4 | B5 | B6 | B7 |
| Metformin (mM) | 8 | 4 | 2 | 1 | 0.5 | 0.25 | 0.125 |
| Number | C1 | C2 | C3 | C4 | C5 | C6 | C7 |
| Sodium butyrate (mM) | 3 | 1.5 | 0.75 | 0.375 | 0.188 | 0.094 | 0.047 |
| Metformin (mM) | 8 | 4 | 2 | 1 | 0.5 | 0.25 | 0.125 |

Figure 2:
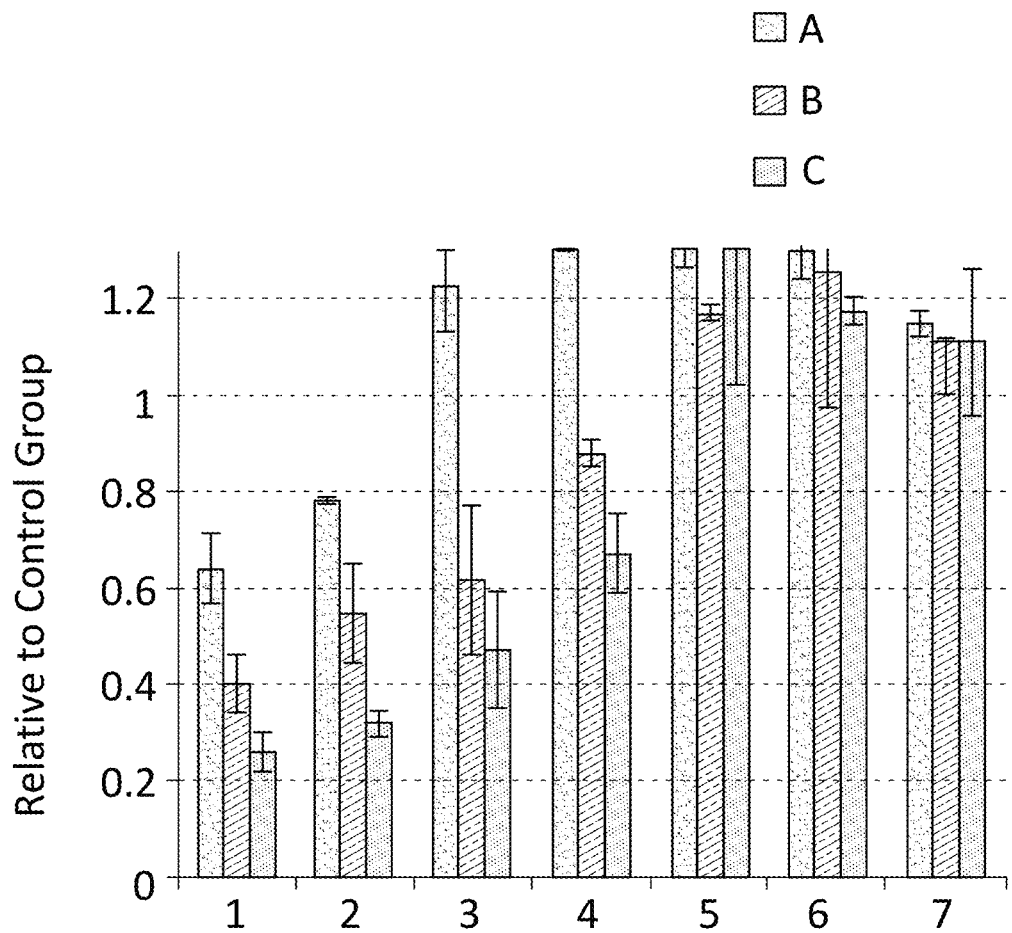
FIG. 2 is a bar chart illustrating the apoptosis results of the treated HCT116 cells analyzed by flow cytometer according to experiment 3.

FIG. 2 is a bar chart illustrating the apoptosis results of the treated HCT116 cells according to experiment 3. With reference to FIG. 2, the different patterns in the bar charts respectively represent A, B, C group, and the numbers at X-axis represent corresponding groups of different concentrations of compounds or pharmaceutical compositions (as shown in above tables), and the numbers at Y-axis represent the ratio of surviving cells in each group relative to the control group. The surviving cells are calculated by the flow cytometer and the analysis software thereof, FACSCalibur.

The bar chart shows that using metformin and sodium butyrate in combination can reduce the survival rate of the HCT116 cells, which is K-ras mutation cell line, and it means the cytotoxic effect is stronger (higher proportion of apoptosis), and better than other groups with individual using metformin or sodium butyrate. Particularly using 0.375 mM to 3 mM of sodium butyrate and 1 mM to 8 mM of metformin in combination has much better synergistic effect. The results show that the pharmaceutical composition produces the better therapeutic efficacy, due to the synergetic effect of metformin and sodium butyrate.

The weight ratio of the metformin to the sodium butyrate is 4:1 (the ratio in molarity is 2.67:1) in the experiments mentioned above, but the present invention is not limited to it. In other experiments, the dose of metformin and sodium butyrate used in combination can be 16 mM of metformin and each concentration thereof 2-fold serially diluted for 7 times, combined with 50 mM of sodium butyrate and each concentration thereof 2-fold serially diluted for 7 times thereof, and any combination thereof.

Details are shown in the following table:

| Metformin (mM) | 16 | 8 | 4 | 2 | 1 | 0.5 | 0.25 |
|---|---|---|---|---|---|---|---|
| Sodium butyrate (mM) | 50 | 25 | 12.5 | 6.24 | 3.12 | 1.56 | 0.78 |

In other words, the dose of using metformin and sodium butyrate in combination can be any combination of each the concentrations, which are showed in the above table. For example, 16 mM metformin can respectively be combined with 50, 25, 12.5, 6.24, 3.12, 1.56 or 0.78 mM sodium butyrate, and other ways of combination are not repeated here. It also offers improving or enhancing therapeutic efficacy to the cancer or tumor patients with K-ras mutation, so the weight ratio of the metformin to the sodium butyrate of the present invention is not necessarily 4:1.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A pharmaceutical composition for treating a cancer patient with K-ras mutation, the pharmaceutical composition comprising an effective amount of metformin and an effective amount of sodium butyrate, wherein the weight ratio of metformin to sodium butyrate is 4:1, and when the pharmaceutical composition is administered to the cancer patient, the metformin and the sodium butyrate offer cooperatively therapeutic efficacy.

2. The pharmaceutical composition according to claim 1, wherein the cancer patient is a lung cancer patient, a pancreatic cancer patient, a rectal cancer patient or a colon cancer patient.

3. The pharmaceutical composition according to claim 1, wherein the metformin and the sodium butyrate act synergistically in treating the cancer patient.

4. The pharmaceutical composition according to claim 1, wherein the metformin is administered at a dose between 130 mg and 1,000 mg, and sodium butyrate is administered at a dose between 40 mg and 300 mg.

5. The pharmaceutical composition according to claim 1, wherein the metformin and the sodium butyrate cooperatively modulate the metabotropic glutamate signaling pathway in cancer cells to treat the cancer patient.

6. A pharmaceutical kit for treating a cancer patient with K-ras mutation, the pharmaceutical kit comprising:

an effective amount of metformin along with a first pharmaceutically acceptable carrier, diluent or excipient; and an effective amount of sodium butyrate along with a second pharmaceutically acceptable carrier, diluent or excipient, wherein, the weight ratio of metformin to sodium butyrate is 4:1, and when the pharmaceutical kit is administered to the cancer patient, the metformin and the sodium butyrate offer cooperatively therapeutic efficacy.

7. The pharmaceutical kit according to claim 6, wherein the cancer patient is a lung cancer patient, a pancreatic cancer patient, a rectal cancer patient or a colon cancer patient.

8. The pharmaceutical kit according to claim 6, wherein the metformin and the sodium butyrate act synergistically in treating the cancer patient.

9. The pharmaceutical kit according to claim 6, wherein the metformin is administered at a dose between 130 mg and 1,000 mg, and the sodium butyrate is administered at a dose between 40 mg and 300 mg.

10. The pharmaceutical kit according to claim 6, wherein the metformin and the sodium butyrate cooperatively modulate the metabotropic glutamate signaling pathway in cancer cells to treat the cancer patient.

* * * * *